US011819355B2

(12) United States Patent
Corsino Espino et al.

(10) Patent No.: US 11,819,355 B2
(45) Date of Patent: Nov. 21, 2023

(54) METHODS AND SYSTEMS FOR AUTOMATIC IMPLANT DETECTION IN MAMMOGRAPHY

(71) Applicant: GE Precision Healthcare LLC, Milwaukee, WI (US)

(72) Inventors: Jorge Corsino Espino, Paris (FR); Olivier Ernoult, Antony (FR); Vincent Jonas Bismuth, Maurepas (FR); Fanny Patoureaux, Beynes (FR); Karima Santi, Maurepas (FR); Maria Belen Aguirre Larrieu, Barcelona (ES)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 162 days.

(21) Appl. No.: 17/375,986

(22) Filed: Jul. 14, 2021

(65) Prior Publication Data
US 2023/0013922 A1    Jan. 19, 2023

(51) Int. Cl.
*A61B 6/00*    (2006.01)
*G06T 7/00*    (2017.01)

(52) U.S. Cl.
CPC .............. *A61B 6/545* (2013.01); *A61B 6/482* (2013.01); *A61B 6/488* (2013.01); *A61B 6/502* (2013.01);
(Continued)

(58) Field of Classification Search
CPC ......... A61B 6/482; A61B 6/488; A61B 6/502; A61B 6/545; A61B 6/544; A61B 6/542; A61B 6/461; A61B 6/405; A61B 6/0414; A61B 6/4035; A61B 6/4283; A61B 6/484; A61B 6/4291; A61B 6/4092; A61B 6/547; A61B 2562/02; A61B 6/468; A61B 6/025; A61B 6/463; A61B 6/469; A61B 6/5217; A61B 6/5235; A61B 6/032; A61B 6/4241;
(Continued)

(56) References Cited

U.S. PATENT DOCUMENTS 8,983,159 B2    3/2015    Tomisaki et al.
10,010,304 B2    7/2018    Morita
(Continued)

FOREIGN PATENT DOCUMENTS

JP    2011010884 A    1/2011
JP    5541989 B2    7/2014

OTHER PUBLICATIONS

"Technology Advances in Mammography Dose Reduction and Image Quality," Available Online at https://www.fujifilmhealthcare.com/sites/default/files/inline-files/FUJIFILM_Cristalle_White_Paper.pdf, Available as Early as Sep. 23, 2020, 5 pages.
(Continued)

*Primary Examiner* — Irakli Kiknadze
(74) *Attorney, Agent, or Firm* — McCoy Russell LLP

(57) ABSTRACT

Various methods and systems are provided for mammogram imaging. In one example, a method for an x-ray mammography system includes determining, based on a pre-exposure image of a subject acquired with the x-ray mammography system before acquisition of one or more main images, that the subject has an implant; automatically adjusting one or more imaging parameters in response to determining that the subject has the implant; and acquiring the one or more main images with the adjusted one or more imaging parameters.

18 Claims, 5 Drawing Sheets

(52) U.S. Cl.
CPC .. *G06T 7/0012* (2013.01); *G06T 2207/10116* (2013.01); *G06T 2207/20081* (2013.01); *G06T 2207/20084* (2013.01); *G06T 2207/30068* (2013.01)

(58) Field of Classification Search
CPC . A61B 6/481; A61B 2034/107; A61B 6/0435; A61B 6/12; A61B 6/5211; A61B 6/5252; A61B 6/582; A61B 6/588; A61B 6/06; A61B 6/465; A61B 6/5205; G06T 7/0012; G06T 2207/10116; G06T 2207/20081; G06T 2207/20084; G06T 2207/30068; G06T 7/0014; G06T 7/0081; G06T 7/0083; G06T 7/0091; G06T 2207/30052; G06T 2207/30096; G06V 10/82; G06V 2201/03; G01T 1/247; G01T 1/246; G01T 1/24; G06K 9/2081; G06K 9/6201; G16H 50/20
USPC ..................................................... 378/37, 62
See application file for complete search history.

(56) References Cited

U.S. PATENT DOCUMENTS

| 10,194,883 | B2 | 2/2019 | Morita |
| 10,219,770 | B2 | 3/2019 | Enomoto et al. |
| 11,344,269 | B2* | 5/2022 | Mertelmeier .......... A61B 6/481 |
| 2008/0002872 | A1 | 1/2008 | Gatesoupe et al. |
| 2009/0136113 | A1* | 5/2009 | Chan ...................... A61B 6/502 |
| | | | 382/132 |
| 2011/0123074 | A1 | 5/2011 | Nie et al. |
| 2020/0261046 | A1* | 8/2020 | Arai ....................... G06T 7/0012 |

OTHER PUBLICATIONS

"Fujifilm Mammography Solution," Fujifilm Website, Available Online at https://www.fujifilm.eu/fileadmin/countries/UK/Medical/brochures/Mammography/XB_1013ER3_AMULET_Innovality.pdf, Retrieved on Jul. 13, 2021, 8 pages.

* cited by examiner

METHODS AND SYSTEMS FOR AUTOMATIC IMPLANT DETECTION IN MAMMOGRAPHY

FIELD

Embodiments of the subject matter disclosed herein relate to mammography, and more particularly, to automatically detecting breast implants during mammography.

BACKGROUND

Mammography is a medical imaging procedure for detecting one or more cancers of a breast. Accurate interpretation of a mammography image (also known as mammogram) and detection of breast cancer relies on generation of high quality mammograms. Many factors may affect the quality of a mammogram. For example, failure to position the breast properly may result in mammographic artifacts and tissue exclusion, and consequently, missed cancers. Further, the presence of breast implants may occlude underlying tissue. The level of training and experience of the technologists can also affect image quality. For example, technologists with less/intermediate training and/or experience may not properly move the implant out of the way during imaging or trigger implant-specific acquisition parameters, and as result, recall rates and missed cancers may be higher.

BRIEF DESCRIPTION

In one embodiment, a method for an x-ray mammography system includes determining, based on a pre-exposure image of a subject acquired with the x-ray mammography system before acquisition of one or more main images, that the subject has an implant; automatically adjusting one or more imaging parameters in response to determining that the subject has the implant; and acquiring the one or more main images with the adjusted one or more imaging parameters.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to automatically detecting/classifying an implant breast prosthesis during a pre-exposure acquisition or main exposure of a breast x-ray exam (e.g., mammogram). One or more images generated from data acquired during the pre-exposure acquisition may be entered into an implant detection model, which is configured to determine whether or not an implant is present, and if so, classify the implant (e.g., as saline or silicone, number of lumens, number of layers, etc.). This detection/classification may trigger an implant workflow where certain information, such as patient information and clinical view name, are autopopulated based on the detection/classification. For example, in a patient record that may be created prior to or during an exam, a field indicative of presence/absence of an implant may be automatically filled based on the implant determination. During the main acquisition, specific image processing/acquisition techniques may be triggered based on the implant determination, which may prevent low quality images from being obtained if the operator of the mammography system forgets or is not aware than the subject has implants. After acquisition, the clinical view name of one or more images may be automatically entered (e.g., implant displaced image versus fully compressed image). Further, if an implant is detected and the user erroneously manually selects incorrect acquisition parameters (such as acquisition parameters better suited for patients without implants), clinical view name, etc., the user may be alerted of missing/erroneous information as "missing implant information" or wrong clinical view name.

Figure 1:
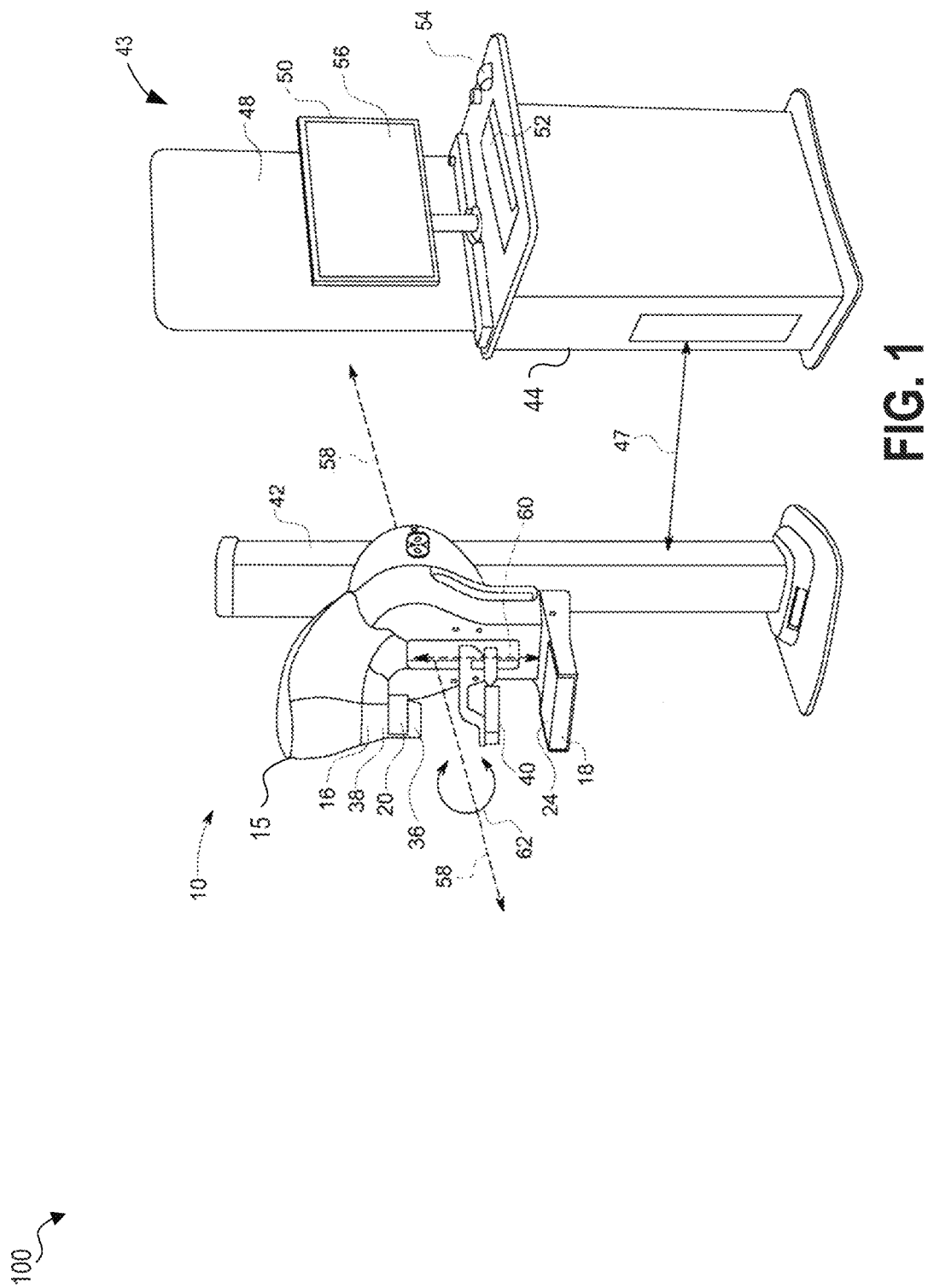
FIG. 1 is a schematic illustration of a mammography system according to an embodiment of the disclosure.

Referring to FIG. 1, a mammography system 100 including an x-ray system 10 for performing a mammography procedure is shown, according to an embodiment of the disclosure. The x-ray system 10 may be a tomosynthesis system, such as a digital breast tomosynthesis ("DBT") system. The x-ray system 10 may be used to perform one or more procedures including digital tomosynthesis imaging and DBT guided breast biopsy. Further, the x-ray system 10 may be utilized to perform a mammography imaging procedure, wherein one or more views including a craniocaudal (CC view) and a mediolateral oblique (MLO view) of a breast are obtained. The x-ray system may be further used to perform other x-ray screening and diagnostic imaging procedures, including contrast-enhanced spectral mammography (CESM), and contrast enhanced DBT (CE-DBT) diagnostic imaging, and interventional procedures, including CESM-guided biopsy and stereotactic procedures.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions about a vertical axis perpendicular to a horizontal detection surface of the detector 18. For example, the angular range of rotation of the radiation source 16 may be −θ to +θ, where θ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications.

The radiation source 16 is directed toward a volume or object to be imaged, and is configured to emit radiation rays at desired times and to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of an object imaged.

In some examples, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure 42 along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The mammography system 100 may further include workstation 43 comprising a controller 44 including at least one processor and a memory. The controller 44 may be communicatively coupled to one or more components of the x-ray system 10 including one or more of the radiation source 16, the radiation detector 18, the compression paddle 40, and a biopsy device. In an example, the communication between the controller and the x-ray system 10 may be via a wireless communication system. In another example, the controller 44 may be in electrical communication with the one or more components of the x-ray system via a cable 47. Further, as shown in FIG. 1, the controller 44 is integrated into workstation 43. In other examples, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 56, a keyboard 52, mouse 54, and/or other appropriate user input devices that facilitate control of the system 10 via a user interface 50.

Through its processors and controllers, the controller 44 may adjust the operation and function of the x-ray system 10. As an example, the controller 44 may control the timing of when the x-ray source 16 emits x-rays, the energy of the x-rays emitted by the x-ray source, and may further adjust how the detector 18 reads and conveys information or signals after the x-rays hit the detector 18, and how the x-ray source 16 and the detector 18 move relative to one another and relative to the body part. The controller 44 may also control how information, including images 42 and data acquired during the operation, is processed, displayed, stored, and manipulated. The different processing steps, including acquiring a pre-exposure image, entering the pre-exposure image to an implant detection model, auto-populating patient fields and/or clinical view fields based on the output of the implant detection model, adjusting one or more actuators of the x-ray system to control operation of the x-ray system, and/or adjusting processing of acquired projection data to form one or more mammogram images, performed by the controller 44, may be provided by a set of instructions stored in non-transitory memory of the processor. Information may also be stored in one or more non-transitory memories of controller 44 for later retrieval and use.

Further, as stated above, the radiation detector 18 receives the radiation rays emitted by the radiation source 16. In particular, during imaging with the x-ray system, a projection image of the imaging body part may be obtained at the detector 18. In some examples, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed via the display portion 50 on the interface 56.

During mammography, the gantry 15 may be adjusted at different angles to obtain images at different orientations, such as a craniocaudal (CC) image and a mediolateral oblique (MLO) view. Further, during obtaining mammography views (e.g., CC and MLO views) the gantry 15, the compression paddle 40, and the detector 18 may be rotated as a single unit about the axis 58. In other examples, the gantry 15 may be rotated about the axis 58 while the compression paddle 40 and the detector 18 remain stationary.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. During tomosynthesis, similar to mammography, the breast is compressed between the compression paddle 40 and the detector 18. The radiation source 16 is then rotated from −θ to +θ, and a plurality of projection images of the compressed breast is obtained at regular angular intervals over the angular range. For example, if the angular range of the x-ray system is ±11 degrees, 22 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional DBT image of the breast.

Furthermore, the x-ray system 10 may be configured to perform a DBT-guided biopsy procedure. Accordingly, in some examples, the system 10 may further include a biopsy device (not shown) comprising a biopsy needle for extracting a tissue sample for further analysis.

Figure 2:
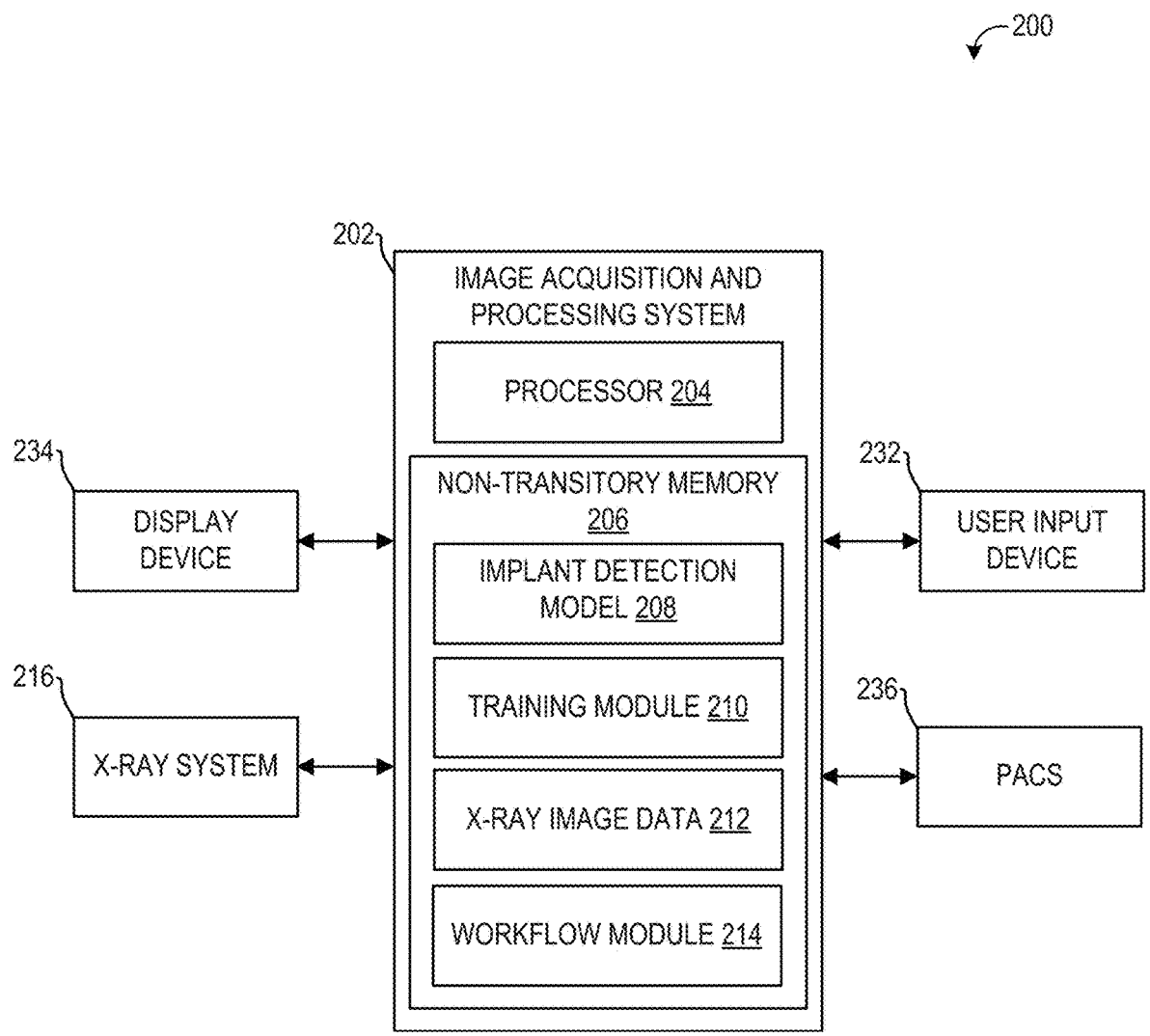
FIG. 2 is block diagram of a mammography system including an implant detection model and workflow module according to an embodiment of the disclosure.

Turning to FIG. 2, a block diagram of a mammography system 200 is shown. The mammography system 200 may be a non-limiting example of the mammography system 100 of FIG. 1. Briefly, the mammography system 200 may be utilized to perform a mammography procedure, such as a routine mammogram, a digital breast tomosynthesis, and/or a biopsy procedure, such as a stereotactic biopsy or DBT-guided biopsy. The mammography system 200 may include an image acquisition and processing system 202, which may be a non-limiting example of controller 44 of FIG. 1. The image acquisition and processing system 202 may include a processor 204 and non-transitory memory 206. Further, the image acquisition and processing system 202 may be operatively coupled to an x-ray system 216, one or more user input devices, such as user input device 232, a display device 234, and one or more image storage systems, such as a picture archive and communication system (PACS) 236.

X-ray system 216 may be an example of x-ray system 10 discussed above with respect to FIG. 1. In an example, the x-ray system 216 may be configured as a medical imaging modality for performing a mammography procedure to image and analyze a body part of a patient, such as a breast. In another example, additionally or alternatively, the x-ray system 216 may be configured for performing a biopsy procedure, such as an x-ray guided biopsy to obtain a tissue sample from the body part of the patient. Further, the x-ray system 216 may be converted from a mammography system for obtaining medical scan images to a biopsy system to perform a biopsy procedure for extracting tissue for evaluation.

The processing system 202 includes the processor 204, which is configured to execute machine readable instructions stored in the non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. According to other embodiments, the processor 204 may include other electronic components capable of carrying out processing functions, such as a digital signal processor, a field-programmable gate array (FPGA), or a graphic board. According to other embodiments, the processor 204 may include multiple electronic components capable of carrying out processing functions. For example, the processor 204 may include two or more electronic components selected from a list of electronic components including: a central processor, a digital signal processor, a field-programmable gate array, and a graphic board. In still further embodiments the processor 204 may be configured as a graphical processing unit (GPU) including parallel computing architecture and parallel processing capabilities.

Non-transitory memory 206 may store an implant detection model 208, a training module 210, x-ray image data, and a workflow module 214. The implant detection model 208 include a machine learning model, such as a deep learning model, comprising a plurality of parameters (including weights, biases, activation functions), and instructions for implementing the one or more deep neural networks to receive image data from the x-ray system 216 and/or processed images from the image acquisition and processing system 202, and determine the presence or absence of an implant (e.g., breast implant) in the image(s). For example, implant detection model 208 may store instructions for implementing a deep learning module comprising one or more neural networks, such as a convolutional neural network (CNN). Implant detection model 208 may include trained and/or untrained neural networks and may further include various data, or metadata pertaining to the one or more neural networks stored therein. Training module 210 may include instructions for training one or more of the deep neural networks stored in implant detection model 208. The training may be performed with a training data set including annotated x-ray images of subjects (where the annotations are input by an expert and/or automatically via patient information stored in an electronic medical record), where each image is annotated to indicate presence or absence of an implant, type of implant (e.g., low absorption material or high absorption material), number of implant lumens, implant surface type (e.g., smooth or textured), whether the image is a compressed breast image or implant-displaced image, etc.

In some examples, the implant detection model 208 may be trained to detect the position of an implant in a breast of a subject, such as relative to a pectoral muscle (e.g., over the pectoral muscle or under the pectoral muscle). In such examples, the instructions to train one or more of the deep neural networks stored in implant detection model 208 may include instructions to perform the training with a training data set including annotated x-ray images of subjects where each image is annotated to indicate the position of the implant (e.g., over or under the pectoral muscle). Likewise, in some examples, the implant detection model 208 may be trained to detect the clinical view of an implant in a breast of a subject, such as whether the implant is displaced (and thus only a small portion of the implant is visible in the image) or not displaced (and thus the full implant is visible, also referred to as a fully compressed view). In such examples, the instructions to train one or more of the deep neural networks stored in implant detection model 208 may include instructions to perform the training with a training data set including annotated x-ray images of subjects where each image is annotated to indicate the clinical view of the implant.

In some examples, the implant detection model 208 may include a first trained network to detect the presence or absence of an implant, a second trained network to detect the implant type (e.g., high or low absorption material), a third trained network to detect the position of the implant, a fourth trained network to detect the clinical view of the implant, and/or other trained networks to detect other features of the implants (e.g., number of lumens, surface type, implant shape). In other examples, two or more of the implant features may be detected by a single trained network. In some embodiments, the training module 210 is not disposed at the image acquisition and processing system 202. The implant detection model 208 thus includes trained and validated network(s).

Non-transitory memory 206 may further store x-ray image data 212. The x-ray image data 212 may include pre-exposure and main exposure images captured by the x-ray system 216. Further, x-ray image data 212 may store x-ray images, ground truth output, iterations of machine learning model output, and other types of x-ray image data that may be used to train the implant detection model 208, when training module 210 is stored in non-transitory memory 206. In some embodiments, x-ray image data 212 may store x-ray images and ground truth output in an ordered format, such that each x-ray image is associated with one or more corresponding ground truth outputs. However, in examples where training module 210 is not disposed at the image acquisition and processing system 202, the images/ground truth output usable for training the implant detection model 208 may be stored elsewhere. As explained above, the ground truth output may include the expert (or otherwise) generated annotations indicating if an implant is present, a type of implant, a positon of the implant, etc. As such, a given training x-ray image may include more than one ground truth output (e.g., implant present, type of implant, position of implant).

The workflow module 214 may receive output from the implant detection model 208 and trigger an implant workflow or a non-implant workflow based on the output of the implant detection model 208. For example, if the implant detection model 208 indicates that a subject being imaged has one or more implants, the workflow module 214 may trigger the implant workflow, such that appropriate patient information fields and clinical view fields may be automatically filled to indicate the subject has implant(s) and/or that implants are present in acquired/reconstructed images. The implant workflow may further include setting or adjusting image acquisition parameters, such that subsequent image/projection information is acquired using an x-ray technique suited for implants (e.g., with a higher kVa and/or mAs than when implants are not present) and/or processing acquired projection data based on the implants and/or implant type (e.g., segmenting the implant to remove the implant from images, reducing saturation and noise caused by the implant, etc.).

Additionally, while not specifically shown in FIG. 2, it is to be understood that in some examples, the image acquisition and processing system 202 may include instructions stored in memory that are executable to process projection data received from the x-ray system 216 to form x-ray images (e.g., mammogram images). The projection data may be processed using one or more suitable reconstruction techniques. Processed images (e.g., mammograms) may be output for display on the display device 234 and/or saved in permanent memory, such as saved in PACS 236.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image acquisition and processing system 202. In one example, user input device 232 may enable a user to make a selection of an x-ray image to use in training a machine learning model, to indicate or label implant stats on images stored the x-ray image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image acquisition and processing system 202 shown in FIG. 2 is for illustration, not for limitation. Another appropriate image processing system may include more, fewer, or different components.

Figure 3:
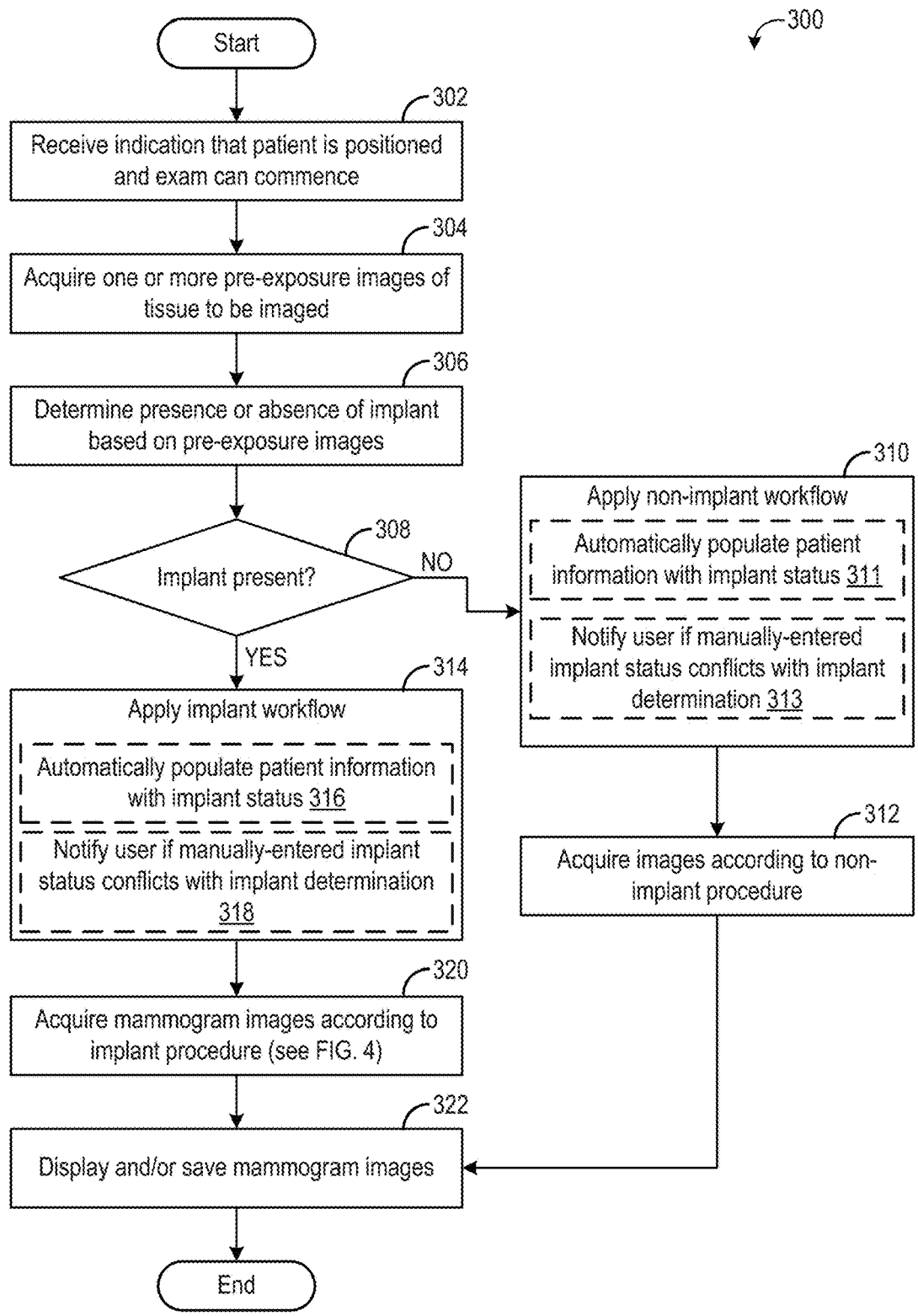
FIG. 3 is a high-level flow chart illustrating a method for performing a mammogram exam on a subject.

Turning to FIG. 3, a high-level flow chart illustrating a method 300 for performing an x-ray imaging session is shown. In particular, the method 300 may be implemented during operation of an imaging system, such as the x-ray system of FIG. 1. Method 300 may be implemented by an image processing system, such as controller 44 at FIG. 1 or image acquisition and processing system 202 of FIG. 2, an edge device connected to the image processing system, a cloud in communication with the image processing system, or any appropriate combination thereof. Method 300 is described with regard to the systems and components of FIG. 1, although it should be appreciated that method 300 may be implemented with other systems and components without departing from the scope of the present disclosure. Further, the method 300 and other methods herein are described with respect to imaging a breast and with respect to the x-ray mammography system discussed at FIG. 1, however, it will be appreciated that the methods and systems for implant detection and system adjustments based on the detected implants described herein may be implemented with other imaging modalities such as x-ray based imaging modalities including CT, DXA, SPECT, etc., and other modalities such as MM, etc., and further implemented during imaging of other body parts that may include implants, such the head (e.g., teeth/mouth), etc.

At 302, an indication is received that a patient has been positioned and an exam can commence. The indication may be received via user input (e.g., an operator of the mammography system may enter a user input via a touch screen, keyboard, etc., indicating that the exam can commence) and/or via commands/sensor input from the mammography system (e.g., the mammography system may include sensors or computer vision to determine that the patient has been positioned such that the exam can commence). In some examples, the indication that the patient is positioned and that the exam can commence may be implied based on a user request to commence imaging (e.g., commence the pre-exposure scan).

At 304, a pre-exposure scan is performed to acquire one or more pre-exposure images of a tissue to be imaged. The pre-exposure scan may be performed with the x-ray source in a single/fixed position (e.g., a medial position, obtained with the x-ray tube positioned at zero degrees from a midline axis perpendicular to the top surface of the detector). The pre-exposure scan may be a lose dose, short exposure scan (e.g., performed at a lower x-ray energy dose and/or for a shorter duration than the main exposure). In some examples, a brightness of the pre-exposure image may be assessed to determine the x-ray technique (e.g., x-ray source current and voltage) for acquiring subsequent (e.g., main exposure) images. The pre-exposure images may be single energy images (e.g., low energy images) or dual energy subtraction images (e.g., where a low energy image and a high energy image are obtained, registered, and then one image is subtracted from the other to remove background). The pre-exposure images may include a target region to be imaged during the main exposure that follows the acquisition of the pre-exposure images, such as a breast to be imaged via one or more mammogram images.

At 306, the presence or absence of an implant in the tissue imaged via the pre-exposure scan is determined based on the one or more pre-exposure images. In one example, the one or more pre-exposure images may be entered as input to an implant detection model, such as the implant detection model 208. The implant detection model may be trained to output a binary indication of the presence of an implant (e.g., an implant is present or an implant is absent) and may output additional information about the implant (when present), such as the type of implant (e.g., low versus high absorption material, number of layers or lumens of the implant), position of the implant, and the clinical view (e.g., whether the implant is compressed/fully present in the images or the implant is displaced). As explained above with respect to FIG. 2, the implant detection model may be a machine learning model, such as one or more neural networks. In other examples, the implant detection model may be a physics-based model that determines the presence or absence of an implant in an image based on the amount of signal attenuation in the pre-exposure images (e.g., an implant may increase signal attenuation).

At 308, method 300 determines if an implant is present in the tissue imaged in the one or more pre-exposure images. If an implant is not present, method 300 proceeds to 310 to apply a non-implant workflow. The non-implant workflow may be applied via a workflow module, such as the workflow module 214 of FIG. 2. The non-implant workflow may include automatically filling any patient information fields specific to implants (e.g., any user interfaces that ask for patient implant status, any DICOM headers or other DICOM information that specifies if implants are present or not) with an indication that the patient does not have an implant in the imaged tissue (e.g., in the imaged breast), as indicated at 311. The patient information fields may be specific to the current x-ray exam. For example, prior to the exam commencing, the operator of the x-ray system or another user may enter patient information via a patient information interface where the patient's name, date of birth, etc., may be entered in order to associate the images that will be taken as part of the exam with the patient. The patient information interface may include an implant status field where the user may specify whether or not the patient has implants. Once the non-implant workflow is triggered, the implant status field may be auto-populated so that the patient is indicated as not having implants, or if the implant status field has already been filled (e.g., manually by the user or based on prior patient information), the non-implant workflow may include notifying the current user (e.g., via a notification displayed on a display device) if the implant status field contradicts the determination that the patient does not have an implant, as indicated at 313. Further, prior to the main exposure commencing, an acquisition parameter interface may be displayed where an operator of the x-ray system or other user may specify certain acquisition parameters for the main exposure, such which breast is being imaged, the imaging plane (e.g., CC), the imaging protocol (e.g., 2D, 3D, CESM, etc.), etc. In at least some protocols, the operator may further be able to select, via the acquisition parameter interface, a setting for the exposure control. If the user has selected an implant-specific setting, the non-implant workflow may output a notification asking the user to confirm that they would like to proceed with the implant-specific exposure control.

At 312, one or more main images (e.g., mammogram images) are acquired according to a non-implant imaging procedure. At least in some examples, the non-implant imaging procedure may include a different x-ray technique than the x-ray technique that is used to acquire images when implants are detected, as will be explained in more detail below with respect to FIG. 4. For example, the x-ray technique may be automatically controlled based on a thickness of the compressed tissue and/or a densest part of the tissue, with x-ray source voltage and current increasing as the thickness and/or density increases. When an implant is not detected, the voltage and/or current may be lower for a given thickness and/or density than when an implant is detected. Additionally, once the image information is acquired, the image information may be processed to generate one or more mammogram images, and the processing may be different when the non-implant procedure is applied relative to when the implant procedure is applied. Regardless of whether an implant is present and the type of implant, the main exposure (from which the mammogram image information is acquired) may include a longer exposure and/or at a higher x-ray dose than the pre-exposure scan. Upon acquiring the images according to the non-implant procedure, method 300 proceeds to 322 to display and/or save the mammogram images. For example, the mammogram images may be displayed on a display device (e.g., display device 234) and/or saved in memory, such as on a PACS (e.g., PACS 236). Method 300 then ends.

Returning to 308, if it is determined that an implant is present (e.g., if the implant detection model outputs an indication that an implant is present in the imaged tissue), method 300 proceeds to 314 to apply an implant workflow. The implant workflow may be applied via the workflow module, similar to the non-implant workflow. The implant workflow may include automatically populating one or more patient information fields with the implant status, as indicated at 316. For example, as explained above, the implant status field of the patient information interface may be automatically filled with an indication that the patient does have an implant. Further, the acquisition parameter interface may be automatically filled such that the implant exposure control is automatically selected.

Applying the implant workflow may also include, as indicated at 318, notifying the user if a manually-entered implant status conflicts with the implant status determined at 306. For example, if the user manually enters "no" to the implant status field of the patient information interface, a notification may be output warning the user that the patient information may be incorrect and/or asking the user to confirm the selected implant status is correct. Likewise, if the user manually selects a non-implant exposure control, a notification may be output warning the user of the potential for poor quality images and/or asking the user to confirm that they want to proceed with the non-implant exposure control.

At 320, one or more mammogram images are acquired according to an implant procedure, which will be described in more detail with respect to FIG. 4. Briefly, the implant procedure may include acquiring image information (e.g., x-ray detector data) of the tissue using the x-ray system with one or more acquisition parameters (e.g., x-ray source voltage, x-ray source current, exposure time, single versus dual energy) selected automatically based on the presence of the implant and/or the implant type. The implant procedure may further include processing the image information based on the presence of the implants and/or type of implant. Upon acquiring the images according to the implant procedure, method 300 proceeds to 322 to display and/or save the mammogram images. For example, the mammogram images may be displayed on a display device (e.g., display device 234) and/or saved in memory, such as on a PACS (e.g., PACS 236). Method 300 then ends. It will be appreciated that method 300 includes imaging of one tissue/region (e.g., breast) and that the method may be repeated for other tissue/regions (e.g., the other breast).

Figure 4:
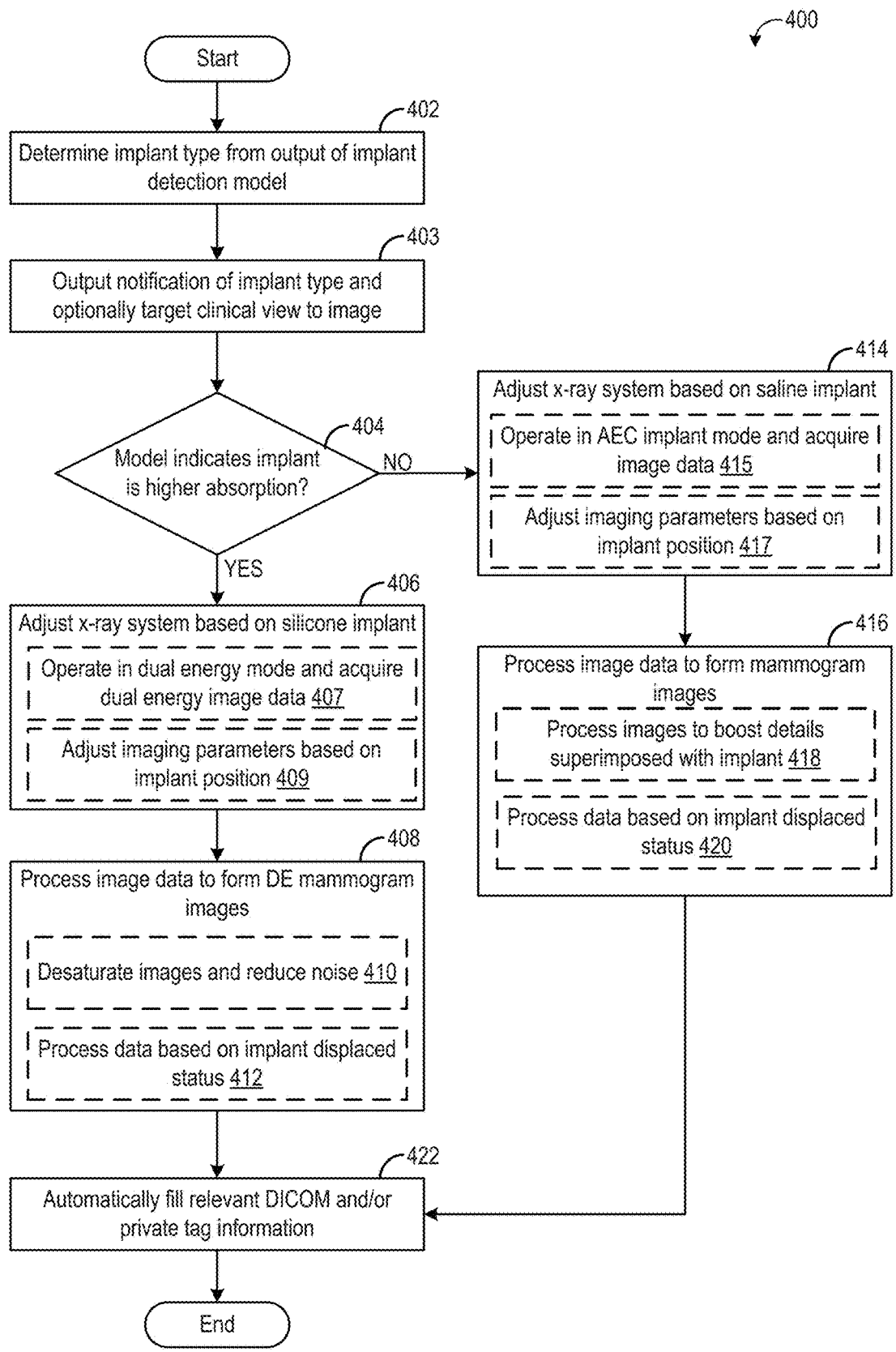
FIG. 4 is a flow chart illustrating a method for adjusting mammography acquisition and/or processing parameters for a subject having breast implants.

FIG. 4 is a flow chart illustrating a method 400 for performing a main exposure to acquire and process one or more mammogram images according to an implant procedure. Method 400 may be implemented during operation of an imaging system, such as the x-ray system of FIG. 1. Method 400 may be implemented by an image processing system, such as controller 44 at FIG. 1 or image acquisition and processing system 202 of FIG. 2. In some examples, method 400 may be carried out as part of method 300, for example as part of acquisition of the mammogram images of 320 of FIG. 3.

At 402, the type of implant present in the tissue to be imaged is determined based on output of the implant detection model. For example, the implant detection model may be trained to determine that an implant is present, and further trained to classify the implant by implant type, such as a higher absorption material (e.g., silicone) implant or a lower absorption material (e.g., saline) implant. The higher absorption material may include implant material that has a higher absorption of x-rays than the lower absorption material. Silicone is an example of a higher absorption material and saline is an example of a lower absorption material, but other implant materials are possible, and the implant detection model may be trained to classify the implant type as higher or lower absorption material based on the amount of signal attenuation provided by the implant. Further, in some examples, the implant detection model may be trained to detect additional features of the implant, such as the position of the implant (e.g., under or over the pectoral muscle), whether the clinical view is a compressed view (where the implant is not displaced) or a displaced view where the implant is displaced out of the main field of view, a number of layers or lumens of the implant, etc. At 403, a notification is output (e.g., for display on the display device and/or to be saved as part of the exam) indicating the implant type and any additional features that are detected. In some examples, the notification may include a recommended clinical view to be imaged. For example, based on the implant type, it may be more preferable to image the tissue in a certain clinical view (e.g., compressed or displaced) and if the detected clinical view is different than the recommended clinical view, the operator may be notified so that the patient can be repositioned, if desired.

At 404, method 400 includes determining if the implant is a higher absorption material implant, based on the type of implant detected at 402. If the implant is a higher absorption material implant, method 400 proceeds to 406 to adjust the x-ray imaging system based on the implant being a higher absorption material implant. Adjusting the x-ray imaging system based on the implant being a higher absorption material implant may include operating the x-ray system in a dual energy mode and acquiring, with the x-ray imaging system, dual energy (DE) image data, as indicated at 407. A dual energy image may be generated from two images, where the two images include a low energy (LE) image acquired with low radiation energy and a high energy (HE) image acquired with high radiation energy. A digital fusion or subtraction process may be used to generate the dual energy (DE) image (also referred to as a combination image) from the LE image and the HE image, such that certain features are better visualized. Operating the x-ray imaging system in the dual energy mode may include operating the x-ray system at a first, lower energy and acquiring x-ray detector data at the first energy level, and then operating the x-ray system at a second, higher energy and acquiring x-ray detector data at the second energy level (or vice versa, where the high energy data is acquired before the low energy data). The higher absorption material (e.g., silicone) has a higher radio-opaqueness than breast tissue or lower absorption material (e.g., saline) implants and thus the x-ray imaging system may be operated in the dual energy mode when a higher absorption material implant is detected, which may increase the visibility of tissue underlying the implant. However, in some examples, rather than operating in the dual energy mode when a higher absorption material implant is detected, the x-ray system may be controlled to operate in a single energy mode. In such examples, the x-ray imaging parameters that are applied may be different than the x-ray imaging parameters applied when the implant is determined to be s lower absorption material (as described below), at least in some examples.

In some examples, the x-ray imaging parameters may be adjusted based on the position of the implant, as indicated at 409. For example, if the implant is determined to be positioned under the pectoral muscle, a different set of x-ray imaging parameters may be used than when the implant is positioned above the pectoral muscle, such as different source voltage or current. However, in other examples, the position of the implant may not affect the x-ray imaging parameters.

At 408, the DE image data is processed to generate one or more DE mammogram images. Processing the DE image data may include generating a low energy (LE) image based on the low energy image data and generating a high energy (HE) image based on the high energy image data, and then generating a DE mammogram image from the LE image and the HE image. This process may include registering the LE and HE images and then performing a fusion or a subtraction process. In some examples, the fusion or subtraction process may include identifying the border of the implant in either or both of the HE and LE images and combining the HE and LE images such that the area that includes the implant in the HE image is combined with the areas outside of the implant in the LE image (e.g., the implant in the LE image is replaced with the implant from the HE image).

Figure 5:
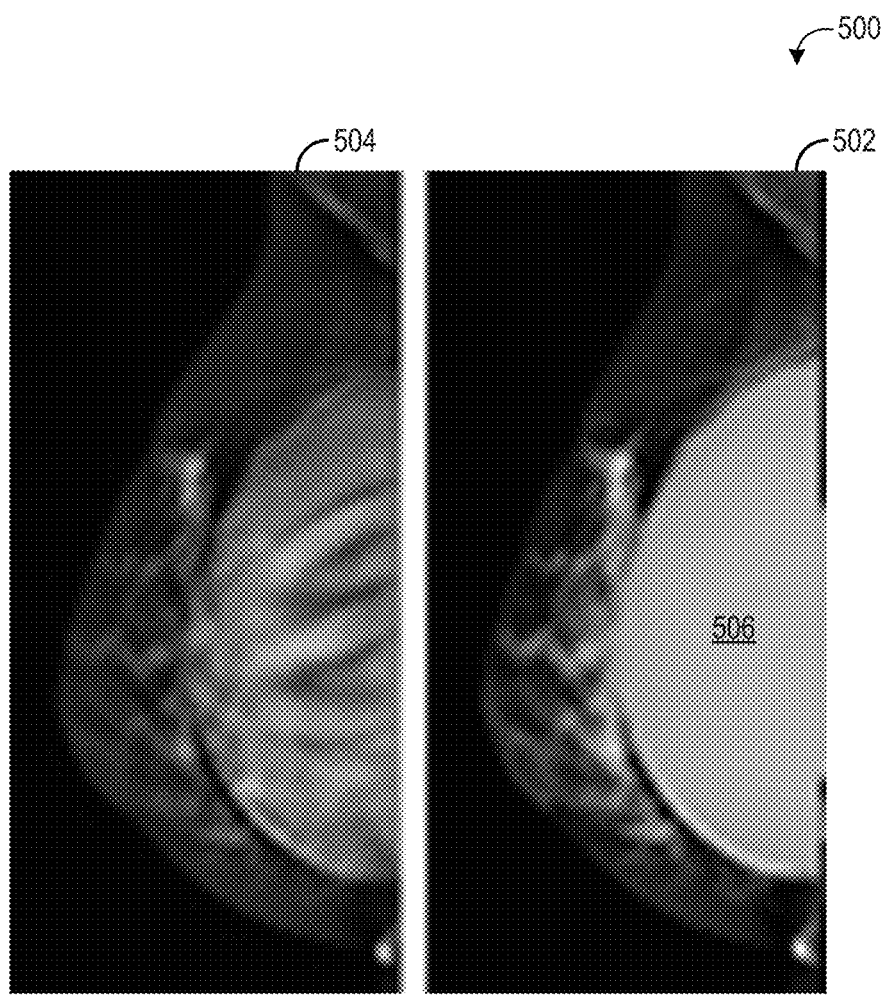
FIG. 5 shows a set of images that may be obtained during a mammography exam on a subject.

For example, FIG. 5 shows a set of images 500 including an LE image 502 and a combined image 504. The combined image 504 is a combination of the LE image and an HE image and includes the LE image with the implant (denoted as implant 506 in the LE image 502) replaced with the implant from the HE image. As appreciated from the combined image 504, the implant may be better visualized when the implant is imaged at high energy, while the surrounding tissue is better visualized when imaged at low energy. In some examples, processing the image data when a higher absorption material implant is detected may include desaturating the resultant images and reducing the noise of the images, as indicated at 410. Due to the high attenuation of silicone implants, photon starvation may occur behind or underneath the implants, and silicone implants tend to produce images that are overly bright, which may make it challenging to detect any anomalous features in the images, such as lesions, microcalcifications, or implant ruptures etc. Thus, the images may be desaturated (when displayed) at least in the area of the implant relative to non-implant images and saline/lower absorption material images and noise inside may be reduced. Further, processing the image data when a higher absorption material implant is detected may include processing the image data based on a displayed view status, as indicated at 412. For example, when the implant detection model determines that the current clinical view is an implant displaced view, a specific image processing routine may be triggered. As an example, if the implant is displaced such that the implant is visible in the image (or only a small portion is visible, such as 10% or less of the implant is visible), the HE and LE images may not be combined and only the LE image may be displayed. Further, any implant-specific processing that is performed to facilitate display/viewing of both the tissue and the implant may be dispensed with and the image may be processed according to standard, non-implant routines.

Returning to 404, if the implant is determined not to be a higher absorption material implant, method 400 proceeds to 414 adjust the x-ray system based on the implant being a lower absorption material implant. This may include operating in a specific mode for imaging implants, herein referred to as automatic exposure control (AEC) for implants, and acquiring x-ray detector data with the x-ray system in the AEC implant mode, as indicated at 415. The x-ray system may be controlled automatically based on the determination that an implant is present, and that the implant is not a higher absorption material implant (and thus is a lower absorption material implant). The AEC implant mode may include adjusting the x-ray source voltage and/or current to be higher in the AEC implant mode than the non-implant AEC mode, for a given tissue thickness and/or density, in an example. In another example, the output from the implant detection model may be used to identify the border of the implant and the area of the image that includes the implant, and the implant could be excluded from the image. In this example, because the implant is going to be excluded from the image, the standard, non-implant exposure control may be applied.

In some examples, the x-ray imaging parameters may be adjusted based on the position of the implant, as indicated at 417. For example, if the implant is determined to be positioned under the pectoral muscle, a different set of x-ray imaging parameters may be used than when the implant is positioned above the pectoral muscle, such as different source voltage or current. However, in other examples, the position of the implant may not affect the x-ray imaging parameters.

At 416, the acquired image data is processed to form one or more mammogram images. The processing of the acquired image data may include processing the images to boost details superimposed with the implant, as indicated at 418. For example, the brightness of the image may be reduced within the implant while being maintained outside the implant. Further, the image may be segmented (e.g., into the implant and non-implant tissue) and different processing techniques applied to the implant relative to the non-implant tissue. Further, processing the image data when a lower absorption material implant is detected may include processing the image data based on a displayed view status, as indicated at 420. For example, when the implant detection model determines that the current clinical view is an implant displaced view, the standard, non-implant image processing routine may be triggered.

At 422, method 400 includes automatically filling relevant DICOM and/or private tag information for each acquired mammogram image (whether the detected implant is a silicone implant or a saline implant). For example, DICOM (which refers to the digital imaging and communications in medicine standard/format) may dictate that all images acquired with particular imaging modalities (such as mammography systems) include an indication of whether the imaged tissue includes an implant. The workflow module may automatically fill this with field based on the determination that the tissue includes an implant, even when the implant is not visible in a given image. Further, as explained above, the implant detection model may be trained to detect attributes of the implant, such as implant type, implant position type (retro-glandular, subfascial, dual-plane, retro-pectoral), clinical view, implant lumen number and material, etc. These attributes may be automatically filled via the workflow module in a private (e.g., non-DICOM) tag so that the information may be available to the operator of the x-ray system as well as other clinicians (e.g., radiologists) who may review the acquired images. Method 400 then returns.

Thus, the embodiments disclosed herein automatically detect/classify implant breast prosthesis during the pre-exposure or main exposure. This detection/classification can help to fill patient information as breast implant presence and clinical view name, trigger specific image processing/acquisition techniques, and alert the operator of the x-ray system of missing/erroneous information as "missing implant information" or the wrong clinical view name.

Previously, conventional mammography systems required, when acquiring a mammography for patients with implant prosthesis, the user to select manually different options in the system as Breast Implant presence (Yes/No) and specific exposure control for implants. Furthermore, these systems may apply a specific image processing when Implant Presence flag is selected. The demand on the user of the imaging system could lead to imaging errors, increasing recall rates and missed detections of anomalous tissue.

Thus, the embodiments disclosed herein employ an implant detection, classification, segmentation, and/or location model in conjunction with a workflow module to help setup the whole system without any user input and present best imaging quality and some extra information to improve user and radiologist workflow.

When the model detects an implant, the workflow module may automatically add patient information as "breast implant present." Further, in the case of a non-automated workflow, the workflow module may prevent user of erroneous input. For example, if the user selects "yes" in the "Implant present?" field when there is no implant on the breast, the workflow module may warn the user, and ask if the user wants to unselect or if the user wants to keep the selection. In such case, the workflow module may ask the user if the image is an "implant displaced image" and fill the view name accordingly. In another example, if an implant is detected but "implant present" not selected, feedback may be provided so that the user may change their selection if the selection was made in error.

The detection of the implant may automatically trigger an implant imaging mode, such as the AEC Implant mode described above. Further, in some examples, the workflow module may prevent imaging in a standard AEC (=AOP) mode when an implant is detected. In doing so, the application of sub-optimal acquisition parameters may be avoided when using manual parameters, avoiding unnecessary retakes.

Further, the model may classify the detected implant by implant type, acquisition compression, implant position, and image appearance. For example, the model may classify the implant as either lower absorption material or higher absorption material (e.g., saline or silicone) and the workflow module may trigger a different processing based on the implant type. Due to high attenuation of silicone implants, there is often photon starvation behind them, and they tend to produce too bright displays. Thus, as explained above, the processing that is applied may desaturate their display and reduce noise inside. Whereas for saline implants that are less radio-opaque, the processing would focus—on the contrary—at boosting details super-imposed with the implants. In some examples, the workflow module may trigger a warning in case of silicone implant where details are lost behind the implant, such as by outputting a notification stating "information superimposed with radiopaque implants may be missed."

In some examples, when an implant is detected, a pilot acquisition may be controlled based on the implant type. The pilot acquisition may detect the densest part of the breast to determine the exposure parameters (e.g., x-ray source voltage and current). When the implant is determined to be a higher absorption material implant, the pilot acquisition may be controlled to avoid the implant in order to optimize the exposure parameters for the breast tissue for the LE image, and the exposure parameters for the HE image may be based on the area including the implant. For lower absorption material implants, the exposure parameters may be optimized for both the breast tissue and the implant, e.g., the densest part of the breast tissue may be identified and the exposure parameters may be identified based on the densest part of the breast tissue, then the exposure parameters may be adjusted based on the implant in order to balance optimized parameters for the breast tissue and the implant. Further, as explained above, different acquisition parameters may be triggered based on the implant type, such as the dual energy imaging in case of very radiopaque implants only (e.g., silicone implants).

The clinical view that is detected (fully compressed or implant displaced) may also trigger different behavior. For example, the workflow module may fill automatically the Clinical view name for "Implant Displaced views" and trigger specific image processing for implant displaced views. The image appearance at the implant border is clinically important and will differ according to implant placement and implant type, which may include by position type (retro-glandular, subfascial, dual-plane, retropectoral) and by number of lumens and material (implants can have one, two, or three lumens made with different material), and this information may be presented to the operator and/or saved as part of the images and/or exam (e.g., as a tag).

In this way, the implant specific imaging mode (e.g., implant AEC) does not need to be selected manually. During pre-exposure image, the implant can be detected and automatically shift the AEC to the implant mode, ensuring best image quality for breast images. When the user does not select Implant AEC, image quality is not ensured and some images need a retake. Further, the implant has higher attenuation than glandular tissue (in particular silicone implants (appearing white)) because the x-rays are not enough to see through. Thus, the implant detection can trigger dual-energy imaging. The current DICOM tag "BreastImplantPresent" may be filled YES for all the patient images. (e.g., the DICOM standard definition: The value is expected to be YES for all images acquired on a breast that contains a breast implant, even when a breast implant is displaced during image acquisition). Detecting the implant by acquisition allows to set the tag by breast and not by patient. During the acquisition, from the different images acquired of the patient, the model can classify which breast has an implant and which does not.

The implant detection and classification and workflow module described herein may help reduce clinical view name errors, as the model may classify images by acquisition type (full compression or implant displaced) the workflow may be accelerated by filling clinical view name without need of predetermined protocols. Additionally, the embodiments described herein may assist to avoid erroneous or sub-optimal acquisition parameters to prevent retakes, optimize image processing as a function of implant material, and optimize image acquisition parameters (e.g., double energy).

A technical effect of the present disclosure includes an improved workflow of imaging technologist and radiologist as the imaging quality will be optimal for breast with implants in terms of exposure parameters and image processing. Another technical effect is that the implant detection model and workflow module may provide the best image quality for implant images, without need of user interaction, prevent user errors in Clinical View Name and Breast Implant presence, and prevent standard exposure control for images including an implant.

The disclosure also provides support for a method for an x-ray mammography system comprising: determining, based on a pre-exposure image of a subject acquired with the x-ray mammography system before acquisition of one or more main images, that the subject has an implant, automatically adjusting one or more imaging parameters in response to determining that the subject has the implant, and acquiring the one or more main images with the adjusted one or more imaging parameters. In a first example of the method, the one or more imaging parameters comprise x-ray source voltage and/or current. In a second example of the method, optionally including the first example, the method further comprises: determining, based on the pre-exposure image, a type of the implant, and wherein automatically adjusting one or more imaging parameters in response to determining that the subject has the implant comprises automatically adjusting one or more imaging parameters based on the type of the implant. In a third example of the method, optionally including one or both of the first and second examples, automatically adjusting one or more imaging parameters based on the type of the implant comprises: increasing an x-ray source voltage and/or current responsive to the implant being a lower absorption material implant, relative to an x-ray source voltage and/or current applied when no implant is present, and acquiring the one or more main images using dual energy imaging responsive to the implant being a higher absorption material implant. In a fourth example of the method, optionally including one or more or each of the first through third examples, acquiring the one or more main images comprises acquiring image data with the x-ray mammography system, and further comprising processing the image data based on the determination that the subject has the implant. In a fifth example of the method, optionally including one or more or each of the first through fourth examples, the method further comprises: determining, based on the pre-exposure image, a type of the implant, and wherein processing the image data based on the determination that the subject has the implant comprises processing the image data based on the type of the implant. In a sixth example of the method, optionally including one or more or each of the first through fifth examples, processing the image data based on the type of the implant comprises applying a first processing technique when the implant is a lower absorption material implant and applying a second processing technique when the implant is a higher absorption material implant. In a seventh example of the method, optionally including one or more or each of the first through sixth examples, the lower absorption material implant is a saline implant and the higher absorption material implant is a silicone implant. In an eighth example of the method, optionally including one or more or each of the first through seventh examples, the method further comprises: determining, based on the pre-exposure image, a position of the implant, and automatically adjusting one or more imaging parameters based on the determined positon of the implant and/or processing the image data based on the determined position of the implant.

The disclosure also provides support for a system, comprising: an x-ray imaging system, and an image acquisition and processing system including instructions stored in memory executable by a processor to: determine, based on a pre-exposure image of a subject acquired with the x-ray imaging system before acquisition of one or more main images, that the subject has an implant, and further determine a type of the implant, automatically adjust one or more imaging parameters of the x-ray imaging system based on the determined type of the implant, and control the x-ray system to acquire the one or more main images with the adjusted one or more imaging parameters. In a first example of the system, the memory stores one or more neural networks, and wherein determining that the subject has an implant, and further determining a type of the implant comprises entering the pre-exposure image as input to the one or more neural networks, wherein the one or more neural networks are trained to output an indication of whether an implant is present in the pre-exposure image, and further trained to output the type of the implant. In a second example of the system, optionally including the first example, the one or more neural networks are further trained to output a clinical view of the implant, where the clinical view of the implant includes the implant being displaced or not displaced, and wherein the instructions are executable to further adjust the one or more imaging parameters based on the clinical view of the implant. In a third example of the system, optionally including one or both of the first and second examples, the one or more neural networks includes a first neural network trained to output the indication of whether the implant is present and the type of the implant and a second neural network trained to output the clinical view of the implant, and wherein the output of the first neural network and the output of the second neural network are each by a workflow module stored in the memory and executed by the processor to automatically adjust the one or more imaging parameters of the x-ray system. In a fourth example of the system, optionally including one or more or each of the first through third examples, the first neural network is trained with a first training set including a first plurality of x-ray images and a first set of ground truth data and the second neural network is trained with a second training set including the first plurality of x-ray images and/or a second plurality of x-ray images and a second set of ground truth data, where the second set of ground truth data includes an indication, for each x-ray image that includes an implant, whether that implant is displaced or not displaced.

The disclosure also provides support for a method for an x-ray mammography system comprising: determining, based on a pre-exposure image of a subject acquired with the x-ray mammography system before acquisition of one or more main images, that the subject has an implant and whether the implant is a lower absorption material implant or a higher absorption material implant, executing a workflow module to automatically fill one or more patient fields of one or more user interfaces based on the determination that the subject has the implant, and acquiring the one or more main images with imaging parameters selected based on the implant being a lower absorption material implant or a higher absorption material implant, including, when the implant is a higher absorption material implant, acquiring dual energy images and when the implant is a lower absorption material implant, acquiring single energy images. In a first example of the method, acquiring the one or more main images comprises acquiring image data with the x-ray mammography system, and further comprising processing the image data based on the implant being a lower absorption material implant or a higher absorption material implant. In a second example of the method, optionally including the first example, the pre-exposure image is acquired with a lower x-ray dose and/or for a shorter exposure than the one or more main images. In a third example of the method, optionally including one or both of the first and second examples, executing the workflow module to automatically fill one or more patient fields of one or more user interfaces based on the determination that the subject has the implant comprises determining that a user has manually indicated, via a patient field of one of the one or more user interfaces, that the subject does not have an implant, and outputting a notification indicating that the subject does have an implant. In a fourth example of the method, optionally including one or more or each of the first through third examples, determining whether the implant is a lower absorption material implant or a higher absorption material implant comprises determining whether the implant is a saline implant or a silicone implant.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an x-ray mammography system comprising:
   determining, based on a pre-exposure image of a subject acquired with the x-ray mammography system before acquisition of one or more main images, that the subject has an implant;
   automatically adjusting one or more imaging parameters in response to determining that the subject has the implant;
   acquiring the one or more main images with the adjusted one or more imaging parameters; and
   determining, based on the pre-exposure image, a type of the implant, wherein automatically adjusting one or more imaging parameters in response to determining that the subject has the implant comprises automatically adjusting one or more imaging parameters based on the type of the implant.

2. The method of claim 1, wherein the one or more imaging parameters comprise x-ray source voltage and/or current.

3. The method of claim 1, wherein automatically adjusting one or more imaging parameters based on the type of the implant comprises:
   increasing an x-ray source voltage and/or current responsive to the implant being a lower absorption material implant, relative to an x-ray source voltage and/or current applied when no implant is present; and
   acquiring the one or more main images using dual energy imaging responsive to the implant being a higher absorption material implant.

4. The method of claim 1, wherein acquiring the one or more main images comprises acquiring image data with the x-ray mammography system, and further comprising processing the image data based on the determination that the subject has the implant.

5. The method of claim 4, wherein processing the image data based on the determination that the subject has the implant comprises processing the image data based on the type of the implant.

6. The method of claim 5, wherein processing the image data based on the type of the implant comprises applying a first processing technique when the implant is a lower absorption material implant and applying a second processing technique when the implant is a higher absorption material implant.

7. The method of claim 6, wherein the lower absorption material implant is a saline implant and the higher absorption material implant is a silicone implant.

8. The method of claim 4, further comprising determining, based on the pre-exposure image, a position of the implant, and automatically adjusting one or more imaging parameters based on the determined position of the implant and/or processing the image data based on the determined position of the implant.

9. A system, comprising:
   an x-ray imaging system; and
   an image acquisition and processing system including instructions stored in a non-transitory memory and executable by a processor to:
      determine, based on a pre-exposure image of a subject acquired with the x-ray imaging system before acquisition of one or more main images, that the subject has an implant, and further determine a type of the implant;
      automatically adjust one or more imaging parameters of the x-ray system based on the determined type of the implant; and
      control the x-ray imaging system to acquire the one or more main images with the adjusted one or more imaging parameters.

10. The system of claim 9, wherein the non-transitory memory stores one or more neural networks, and wherein determining that the subject has an implant, and further determining a type of the implant comprises entering the pre-exposure image as input to the one or more neural networks, wherein the one or more neural networks are trained to output an indication of whether an implant is present in the pre-exposure image, and further trained to output the type of the implant.

11. The system of claim 10, wherein the one or more neural networks are further trained to output a clinical view of the implant, where the clinical view of the implant includes the implant being displaced or not displaced, and wherein the instructions are executable to further adjust the one or more imaging parameters based on the clinical view of the implant.

12. The system of claim 11, wherein the one or more neural networks includes a first neural network trained to output the indication of whether the implant is present and the type of the implant and a second neural network trained to output the clinical view of the implant, and wherein the output of the first neural network and the output of the second neural network are each by a workflow module stored in the non-transitory memory and executed by the processor to automatically adjust the one or more imaging parameters of the x-ray system.

13. The system of claim 12, wherein the first neural network is trained with a first training set including a first plurality of x-ray images and a first set of ground truth data and the second neural network is trained with a second training set including the first plurality of x-ray images and/or a second plurality of x-ray images and a second set of ground truth data, where the second set of ground truth data includes an indication, for each x-ray image that includes an implant, whether that implant is displaced or not displaced.

14. A method for an x-ray mammography system comprising:
   determining, based on a pre-exposure image of a subject acquired with the x-ray mammography system before acquisition of one or more main images, that the subject has an implant and whether the implant is a lower absorption material implant or a higher absorption material implant;
   executing a workflow module to automatically fill one or more patient fields of one or more user interfaces based on the determination that the subject has the implant; and
   acquiring the one or more main images with imaging parameters selected based on the implant being a lower absorption material implant or a higher absorption material implant, including, when the implant is a higher absorption material implant, acquiring dual energy images and when the implant is a lower absorption material implant, acquiring single energy images.

15. The method of claim 14, wherein acquiring the one or more main images comprises acquiring image data with the x-ray mammography system, and further comprising processing the image data based on the implant being a lower absorption material implant or a higher absorption material implant.

16. The method of claim 14, wherein the pre-exposure image is acquired with a lower x-ray dose and/or for a shorter exposure than the one or more main images.

17. The method of claim 14, wherein executing the workflow module to automatically fill one or more patient fields of one or more user interfaces based on the determination that the subject has the implant comprises determining that a user has manually indicated, via a patient field of one of the one or more user interfaces, that the subject does not have an implant, and outputting a notification indicating that the subject does have an implant.

18. The method of claim 14, wherein determining whether the implant is a lower absorption material implant or a higher absorption material implant comprises determining whether the implant is a saline implant or a silicone implant.

* * * * *